United States Patent [19]

Cadogan et al.

[11] Patent Number: 4,827,010

[45] Date of Patent: May 2, 1989

[54] CYCLIC PHOSPHONIC MONOESTERS AND THEIR PREPARATION

[75] Inventors: John I. G. Cadogan, Richmond, England; Ian Gosney, Edinburgh, Scotland; Peter M. Wright, deceased, late of Duffield, England, by Susan J. Wright, legal representative

[73] Assignee: The British Petroleum Company p.l.c., London, England

[21] Appl. No.: 89,301

[22] Filed: Aug. 25, 1987

[30] Foreign Application Priority Data

Aug. 3, 1986 [GB] United Kingdom ................. 8621044

[51] Int. Cl.⁴ ............................................. C07F 9/38
[52] U.S. Cl. ...................................... 558/82; 524/117; 252/609
[58] Field of Search .......................... 558/82; 524/117; 252/609

[56] References Cited

U.S. PATENT DOCUMENTS 4,317,769  3/1982  Saito et al. ............................. 558/82
4,439,564  3/1984  Chasar ................................... 558/82

OTHER PUBLICATIONS

Cadogan et al.; "Thermally Induced Gas Phase Phosphonylation of Arenes via Intramolecular Trapping of an Aryl Metaphosphate Moiety"; J. Chem. Soc. Chem. Commun.; 1986, (23), 1685-6, (Eng.).

*Primary Examiner*—Jacqueline V. Howard
*Attorney, Agent, or Firm*—Brooks Haidt Haffner & Delahunty

[57] ABSTRACT

A process for preparing cyclic phosphonic monoesters comprising subjecting aryloxyphosphines of defined formulae to flash pyrolysis, is provided. The aryloxyphosphines are those having the general formula

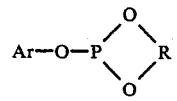

where Ar is aryl and R is a hydrocarbyl radical capable of forming unsaturated hydrocarbon on severance of the C—O linkages.

4 Claims, 1 Drawing Sheet

U.S. Patent May 2, 1989 4,827,010
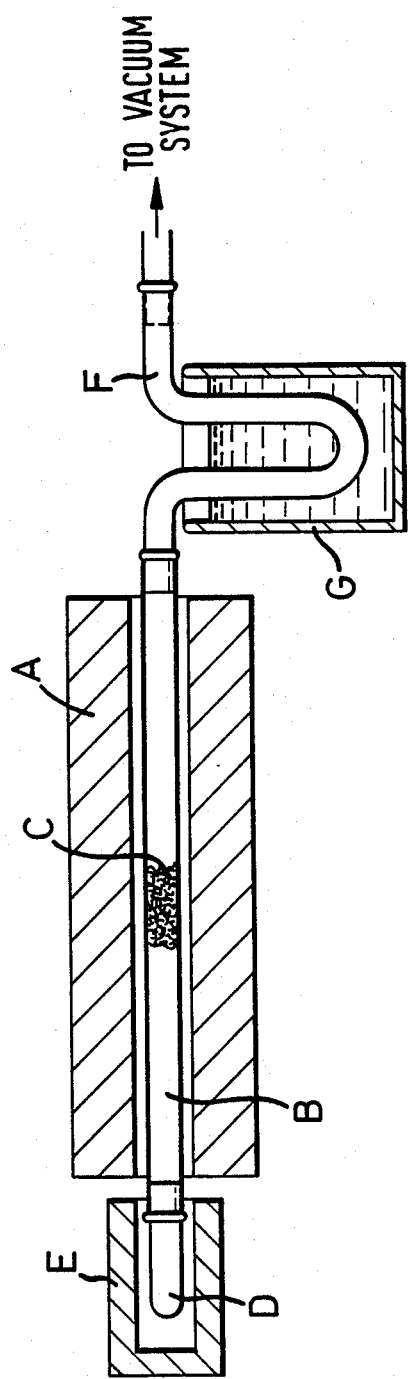

CYCLIC PHOSPHONIC MONOESTERS AND THEIR PREPARATION

This invention relates to a method of preparing cyclic phosphonic monoesters and to certain novel monoesters which may be prepared by the method.

Cyclic phosphonic monoesters having the general formula

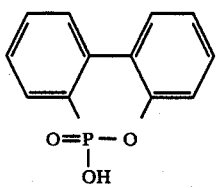

are known. They and/or their alkaline earth metal salts can impart heat and fire resistance to polymers. (See, for example, Chemical Abstracts Vol 89 (1978) page 30 Abstract 147636L and Belgian Patent Specification No. 882283). In Belgian Patent Specification No. 882283, the hydrogens of the aryl rings can be substituted by halogen, CN, acyl, alkyl (optionally substituted), aryl (optionally substituted) or aralkyl and the compounds can be prepared by dehydrogenating the corresponding di-acid compound.

The method of preparation of the present invention uses as starting compounds aryloxyphosphites.

According to the present invention a method of preparing cyclic phosphonic monoesters comprises subjecting an aryloxyphosphite having the general formula,

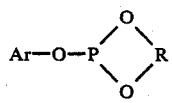

where Ar is aryl and R is a hydrocarbyl radical capable of forming an unsaturated hydrocarbon on severance of the C—O linkages, to flash pyrolysis.

The flash pyrolyis is preferably flash vacuum pyrolysis, a technique which is typically carried out under the following ranges of conditions

| | |
|---|---|
| Temperature | 400 to 950° C., preferably about 800° C. |
| Pressure | 0.01 to 10 mmHg, preferably about 0.01 mmHg |
| Time | 0.001 to 10 sec, preferably about 0.01 sec |

Flash vacuum pyrolysis is a generally known technique, described for example, by R. F. C. Brown in 'Pyrolytic Methods in Organic Chemistry', Academic Press, London, 1980.

The other main product of the reaction when R is $C_2H_4$ is ethylene so it is postulated that the general reaction generates a highly electrophilic metaphosphate ($ArOPO_2$) moiety which cyclises by an intra-molecular C—H insertion reaction.

The Ar radical of the oxyphosphite should have carbon atoms at a suitable spacing to give a ring structure with the phosphorus and oxygen atoms. Thus it may be a two (or more) membered aryl radical (e.g. napthyl) or two aryl rings linked by alkyl (e.g. a benzyl methane radical). It may also be an alkyl substituted benzyl radical (e.g. a tri-tertiary butyl benzene radical).

The hydrogens of the phenyl rings of the Ar radical may be substituted by halogen, acyl, alkyl, CN, or $NO_2$.

The aryl oxyphosphites may be defined generally as 2-aryloxy-1,3,2-dioxaphospholanes. The R should be a hydrocarbyl radical that readily forms an unsaturated hydrocarbon when the C—O linkages are severed. R is preferably

converting, as indicated above, to ethylene during the reaction. It may also be

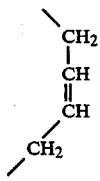

converting to butadiene, or

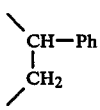

converting to styrene.

The preferred aryloxyphosphites may be prepared by mixing the appropriate phenol with equimolar amounts of 2-chloro-1,3,2-dioxaphospholane and $Et_3N$ in dry benzene, or, alternatively, by reaction of the phenol with $PCl_3$ and addition of an equimolar amount of ethylene glycol in the presence of $Et_3N$. The desired aryloxyphosphites may be recovered by filtration, removal of solvent and distillation, as colourless, hygroscopic liquids.

Particular Ar groups of the aryloxyphosphite and the monoester products produced from such phosphites include

| Ar Group | Monoester Product |
|---|---|
| 1(a) 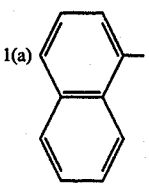 | (2) 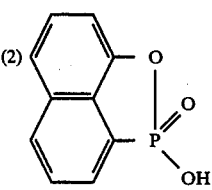 |

-continued

| Ar Group | Monoester Product |
|---|---|
| 1(b) 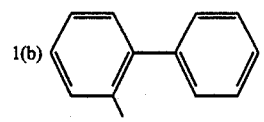 | (3) 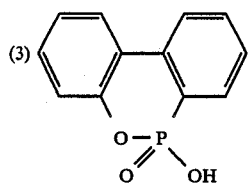 |
| 1(c) 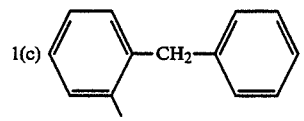 | (4) 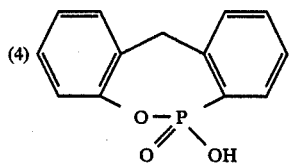 |
| 1(d) 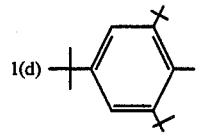 | (5) 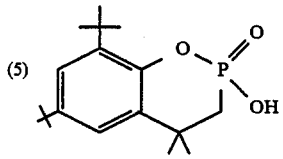 |

The monoester products may be defined chemically as
(2) 2-hydroxy-2H-naphth [1,8-c,d]-1,2-oxaphosphol-2-one
(3) 6-hydroxy-6H-dibenz[c,e]-1,2-oxaphosphorin-6-one
(4) 6-hydroxy-6,11-dihydro-dibenz [c,f]-1,2-oxaphosphepin-6-one
(5) 6,8-di-t-butyl-2-hydroxy-4,4-dimethyl-3,4-dihydro-2H-benz-1,2-oxaphosphorin-2-one Compound (3) is the known compound described in the opening paragraphs of this Specification.

Compounds (2), (4) and (5) have, however, as far as is known, not been previously described. Accordingly, the present invention includes as novel compounds per se compounds (2), (4) and (5) having the formulae set out previously.

The monoester products can be recovered as colourless solids in good yield from flash vacuum pyrolysis reaction products by leaching with anhydrous aprotic solvents.

The monoester products can be readily hydrolysed to phenolic phosphonic acids using aqueous alkaline solutions.

If the Ar radical of the aryloxy phosphite contains an abstractable beta-hydrogen,, the reaction under the same flash vacuum pyrolysis conditions follows a different pathway. Ethylene is eliminated, but the metaphosphate intermediate rearranges with the loss of $HPO_3$. Thus with Ar as 1(e)
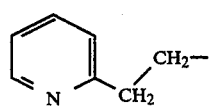

or

1(f)
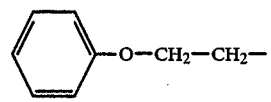

the reaction proceeds according to the equation

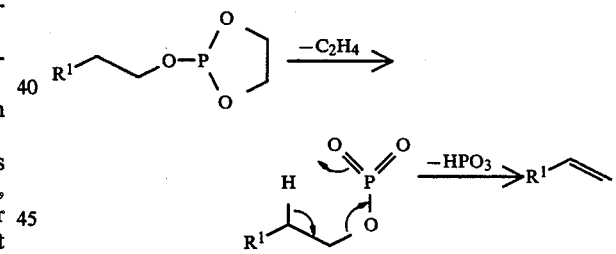

R being pyridyl for 1(e) and phenoxy for 1(f) to give, from (e), 2-vinyl pyridine and, from (f), phenyl vinyl ether.

The reaction may conveniently be carried out in the apparatus described in FIG. 1, in which a Furnace A contains a silica tube B which may be packed with short lengths of silica tubing C. The presence of the silica tubing C reduces the minimum temperature required for complete decomposition of a compound in one pass by 50°–100° C., and hence increases contact time. One end of the silica tube is fitted with an inlet tube D contained in an oven E. The other end of the silica tube is connected to a vacuum system by means of a U-tube trap F which is immersed in a liquid nitrogen bath G. In operation, the furnace A is pre-heated to the desired temperature, following which the oven E is heated to the sublimation point of the substrate, which is contained in the inlet tube D. The product of the reaction is collected in the trap F.

The invention is illustrated by the following examples.

EXAMPLE 1–4

Preparation of Cyclic Phosphonic Monoesters

Various aryloxyphosphites, prepared as described previously, were subjected to flash vacuum pyrolysis in the equipment described above and under the following conditions.

| Furnace inlet temperature | 100–200° C. |
|---|---|
| Furnace temperature | 800° C. |
| Exit trap temperature | −72 to −192° C. (cooled by liquid nitrogen) |
| Vacuum | 0.01 mmHg |
| Residence Time | 0.01 seconds |

The reaction products were isolated by leaching the exit trap with an anhydrous aprotic solvent, the monoester products being recovered as colourless solids. Identification of the products was by $^2$H, $^{13}$C and $^{31}$P n.m.r., i.r., and mass spectral and microanalytical data.

The following results were obtained

| Example | Feedstock | Product | Molar Yield % | Product Characteristics |
|---|---|---|---|---|
| 1 | 1(a) | (2) | 50 | m.p 192° C. (decomp. temp.) 31p δ (CD$_3$)$_2$SO 27.16 |
| 2 | 1(b) | (3) | 74 | m.p 203–4° C. 31p δ (CD$_3$)$_2$SO 6.04 |
| 3 | 1(c) | (4) | 45 | m.p 211–15° C. 31p δ (CD$_3$)$_2$SO 8.40 |
| 4 | 1(d) | (5) | 90 | m.p 198–201° C. 31p δ (CD$_2$Cl$_2$) 29.79 |

EXAMPLE 5

Hydrolysis to Phenol Phosphonic Acid 1 g of product (2) was added to 50 ml of saturated aqueous sodium bicarbonate solution at room temperature and stirred for 2 hours. The reaction product was isolated by filtration, after acidification of the solution to pH1 with conc. HCL, giving an almost quantitative yield of the phenol phosphonic acid (m.p. 242°–246° C.; 31pδ(CD$_3$)$_2$SO 19.07).

EXAMPLES 6–7

Preparation of Vinyl Compounds

Example 1 was repeated using as feedstock compounds 1(e) and 1(f). The products were isolated by distillation under vacuum.

The following results were obtained

| Example | Feedstock | Product | Molar Yield |
|---|---|---|---|
| 6 | 1(e) | 2-vinyl pyridine | Quantitative |
| 7 | 1(f) | phenyl vinyl ether | Quantitative |

In addition to ethylene as a by-product, there was also the formation of a glassy solid with all the properties expected for polymeric metaphosphoric acid.

We claim:

1. A method of preparing cyclic phosphonic monoesters comprising subjecting an aryloxyphosphite of the general formula

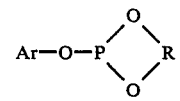

(where Ar is aryl and R is a hydrocarbyl radical capable of forming an unsaturated hydrocarbon on severance of the C–O linkages) to flash vacuum pyrolysis under a temperature of 400° to 950° C., pressure of 0.01 to 10 mmHg and time of 0.001 to 10 sec, and recovering a cyclic phosphonic monoester product.

2. A method as claimed in claim 1, wherein R is

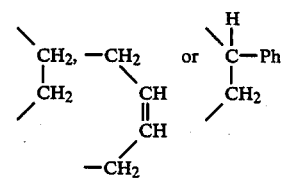

3. A method as claimed in claim 2, wherein R is

Ar is one of the following:

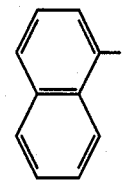

(a)

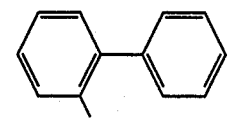

(b)

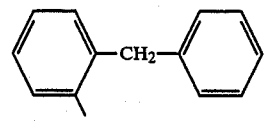

(c)

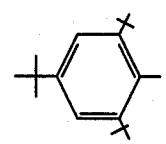

(d)

and the respective cyclic phosphonic monoesters products have the formulae:

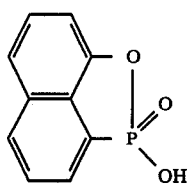 (2)
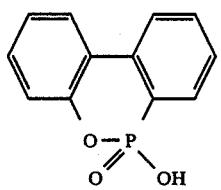 (3)
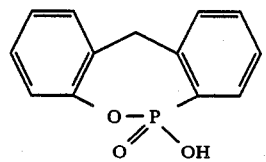 (4)
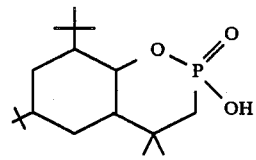 (5)
4. A cyclic phosphonic monoester having the formula of compound (2), (4), or (5) as defined in claim 3.
* * * * *

UNITED STATES PATENT AND TRADEMARK OFFICE
CERTIFICATE OF CORRECTION

PATENT NO. : 4,827,010

DATED : May 2, 1989

INVENTOR(S) : John I.G. Cadogan, et al

It is certified that error appears in the above-identified patent and that said Letters Patent is hereby corrected as shown below:

Col. 1, line 35, the comma should be deleted after "mula"

Col. 1, line 41, there should be a comma before the word "where"

Col. 2, l. 6, correct the spelling of "naphthyl"

Col. 3, l. 56, there should be only one comma after "beta-hydrogen,

Signed and Sealed this

Thirtieth Day of January, 1990

*Attest:*

JEFFREY M. SAMUELS

*Attesting Officer*   Acting Commissioner of Patents and Trademarks